United States Patent [19]

Cleator

[11] Patent Number: 5,747,344
[45] Date of Patent: May 5, 1998

[54] DEVICE AND METHOD FOR SCREENING FECAL OCCULT BLOOD SPECIMENS

[76] Inventor: Iain G.M. Cleator, 1051 Laurier Avenue, Vancouver, B.C., Canada, V6 H1Y2

[21] Appl. No.: 658,543

[22] Filed: Jun. 5, 1996

[51] Int. Cl.⁶ .................................................. G01N 33/72
[52] U.S. Cl. .................. 436/66; 422/55; 422/56; 422/57; 422/58; 422/61
[58] Field of Search ................... 422/55, 56, 57, 422/58, 61; 436/66

[56] References Cited

U.S. PATENT DOCUMENTS

| | | | |
|---|---|---|---|
| 3,996,006 | 12/1976 | Pagano | 23/253 |
| 4,225,557 | 9/1980 | Hartyl et al. | 422/56 |
| 4,259,964 | 4/1981 | Levine | 422/61 |
| 4,365,970 | 12/1982 | Lawrence et al. | 422/58 |
| 4,367,750 | 1/1983 | Levine | 422/61 |
| 4,578,358 | 3/1986 | Oksman et al. | 436/66 |
| 4,645,743 | 2/1987 | Baker et al. | 436/66 |
| 4,742,002 | 5/1988 | Guadagno | 435/28 |
| 4,789,629 | 12/1988 | Baker et al. | 435/7 |
| 4,808,379 | 2/1989 | Wardlow et al. | 422/56 |
| 5,100,619 | 3/1992 | Baker et al. | 422/58 |
| 5,106,582 | 4/1992 | Baker | 422/58 |
| 5,171,529 | 12/1992 | Schreiber | 422/58 |
| 5,182,191 | 1/1993 | Fam | 422/61 |
| 5,196,167 | 3/1993 | Guadagno et al. | 422/56 |
| 5,238,847 | 8/1993 | Steinbiss et al. | 422/61 |
| 5,264,181 | 11/1993 | Schreiber | 422/58 |
| 5,310,680 | 5/1994 | Baker et al. | 436/66 |
| 5,391,498 | 2/1995 | Baker et al. | 436/66 |

OTHER PUBLICATIONS

Jack S. Mandel, John H. Bond, Timothy R. Church, Dale C. Snover, G. Mary Bradley, Leonard M. Schulman and Fred Ederer, "Reducing Mortality From Colorectal Cancer By Screening For Fecal Occult Blood", The New England Journal of Medicine, vol. 328, May 13, 1993, No. 19, 7 pages.

Sidney J. Winawer, "Colorectal Cancer Screening Comes of Age", The New England Journal of Medicine, vol. 328, May 13, 1993, No. 19, pp. 1416 and 1417.

*Primary Examiner*—Jill Warden
*Assistant Examiner*—Sharidan Carrillo
*Attorney, Agent, or Firm*—Nixon & Vanderhye

[57] ABSTRACT

A specimen testing device having first and second panels and a reagent sheet therebetween. The first panel has an aperture with a cover and the second cover has an aperture opposite the aperture in the first panel. The sheet in the first aperture has first and second portions disposed on opposite sides of a longitudinal axis of the panel and a fecal specimen is smeared on the sheet in the apertures so as to cover the first and second portions. The second panel is provided with a cover which overlies the first portion of the sheet and with a further cover which overlies the second portion of the sheet. The further cover is selectively moveable depending on the outcome of testing of the sample on the first portion through the respective aperture on the second panel.

13 Claims, 3 Drawing Sheets

DEVICE AND METHOD FOR SCREENING FECAL OCCULT BLOOD SPECIMENS

The present invention relates to a device for determining the presence of occult blood in fecal matter, and to a method of testing using such a device.

BACKGROUND OF THE INVENTION

For many years it has been recognized that colorectal cancer and large polyps bleed into the stool. Use of guaiacum for the detection of blood was described in "The Scarlet Letter" by Sherlock Holmes as being sensitive but unreliable. The problem has been that guaiacum detects oxidizing agents of which blood is only one, and red meat and other oxidizing agents also can test positive.

A typical form of fecal occult blood testing known as Haemoccult II utilizes a guaiac treated test sheet upon which a specimen of fecal material is smeared. A developing solution is applied to the opposite side of the sheet yielding a blue color which suggests that blood may be present in the fecal specimen. The drawback of this approach is that a high percentage of false positives is obtained from patients who in fact do not have a cancer or polyp. A false positive result in the test often results in expensive testing of patients who in fact have simply consumed a lot of meat just prior to the test.

One approach to overcome the high incidence of false positives has been to make the test paper sensitive enough to detect up to 2% of blood but not sensitive enough to produce too many false positives. A disadvantage of this compromise approach is that because of the reduced sensitivity, a number of cancers and polyps are not detected.

In an effort to increase sensitivity, the Haemoccult Sensa system was devised. However, this system results in a higher incidence of false positives requiring unnecessary invasive tests.

Alternative approaches to cutting down on false positives have involved placing patients on specific diets designed to restrict intake of animal proteins and other sources of false positives. Despite these efforts, large numbers of false positives still occur. One reason for this is the very long time it can take for food to pass through the bowel in certain patients.

A specific test for human hemoglobin has been devised. This test—the Haemselect test—theoretically registers only human hemoglobin and not animal blood from meat or other agents and therefore theoretically does not require the patient to be on a special diet. Another possible advantage is that human blood from the upper gastrointestinal tract may be digested by the time it reaches the stool and the only human blood detected would be that from the distal bowel. A serious drawback of the Haemselect test is that it is expensive for a screening test and requires specially trained individuals to perform and read the test.

A need therefore exists for an inexpensive and easy-to-use test which has a minimal incidence of false positives and can be readily used in a doctor's office. The invention of the present application meets that need.

SUMMARY OF THE INVENTION

In accordance with one aspect of the present invention, there is provided a testing device including a first panel, a first aperture in the first panel, a second panel and a second aperture in the second panel opposite the first aperture. A sheet is deposed between the first and second panels for receiving a specimen through the first aperture. The sheet has first and second portions disposed on opposite sides of a longitudinal axis of the first panel onto which the specimen is placed. A first aperture cover is mounted on the first panel and overlies the first aperture. A second aperture cover is mounted on the second panel and overlies the first portion of the sheet. A third aperture cover is also mounted on the second panel and overlies the second portion of the sheet. The second and third covers are movable independently of each other to selectively expose the first and second portions of the sheet.

According to a preferred aspect, the first and second apertures are rectangular and extend transversely across the first and second panels. The first cover is preferably hingedly mounted along a hinge line extending transversely of the first panel, and the second cover is preferably hingedly mounted along a hinge line extending longitudinally of the second panel. The third cover is preferably hingedly mounted along a hinge line extending longitudinally of the second panel.

The sheet may be a single piece of paper, typically filter paper, with a hydrophobic dividing strip separating the first and second portions to prevent or minimize possible leakage of developing solution from the first portion to the second portion. Alternatively, the first and second portions may be comprised of two separate pieces of filter paper separated by a hydrophobic barrier. The paper sheet may be impregnated with reagent (e.g. guaiac) over the entire area thereof, or may be impregated with reagent (guaic) only on the first portion and plain unimpregnated filter paper for the second portion. The hydrophobic material may be wax or other suitable solid organic material.

In another preferred aspect, the first and second portions are provided with indicating means for locating where specimen is to be placed on the sheet through the first aperture and where developing solution is to be placed on the first portion through the second aperture. At least one of the indicating means, usually that in the second portion, is preferably comprised of a perforated zone which is removable from the sheet. Preferably, the third cover overlies the removable zone.

In accordance with a particularly preferred aspect of the invention, the first panel has three apertures extending transversely of the first panel and the second panel has two apertures opposite the three apertures which extend longitudinally of the second panel. A support panel for the sheet is provided between the first and second panels with apertures corresponding to the apertures in the first panel. Each of the three apertures in the first panel has a respective cover hingedly mounted along a hinge line extending transversely of the longitudinal axis of the panel and overlying a respective aperture and respective first and second portions of the sheet. A single second cover is hingedly mounted on the second panel along a hinge line extending longitudinally of the second panel and overlies the three first portions. A single third cover is hingedly mounted on the second panel along a hinge line extending longitudinally of the second panel and overlies the three second portions. The second and third covers are selectively movable with respect to each other to expose the first and second portions as desired.

According to another preferred feature, the device may carry printed matter on the first panel such as patient details and instructions for opening of the respective covers to reveal the apertures on which the specimen is smeared. Printed matter may also be provided on the second panel, such as instructions to the doctor for conducting testing of specimens.

A further preferred feature of the device is that sticking of the cover to the specimen is prevented by providing the inside surfaces of the respective aperture covers with a non-stick coating, such a wax layer.

According to yet another aspect of the invention, there is provided a method of analyzing a specimen using a specimen testing device according to the invention. The method includes the steps of obtaining a specimen, for example a fecal specimen, opening an aperture cover on the first panel, smearing a portion of the specimen on the first and second portions of the sheet through the first aperture, and closing the first aperture cover to overlie the aperture and the specimen on the sheet. A first analysis of the specimen is carried out by opening the aperture cover on the second panel to expose the first portion of the sheet carrying the specimen and applying a reagent to the exposed first portion through the second panel. Depending on the outcome of the first analysis, the other aperture cover on the second panel is selectively opened to expose the second portion of the sheet carrying the specimen and further analysis is carried out, for example in a laboratory.

The present invention enjoys numerous advantages. In particular, the device is embodied in one card which readily facilitates transference between the doctor and the patient and between the doctor and another testing location, such as a laboratory. The device is easy to use by the patient and is inexpensive to produce. A particularly important advantage is that the device allows a first test to be carried out by the doctor and, in the event that a specimen is positive, subsequent testing can be carried out on the same specimen.

BRIEF DESCRIPTION OF THE DRAWINGS

The invention will now be described with reference to the accompanying drawings, in which.

DETAILED DESCRIPTION OF PREFERRED EMBODIMENTS

Figure 1:
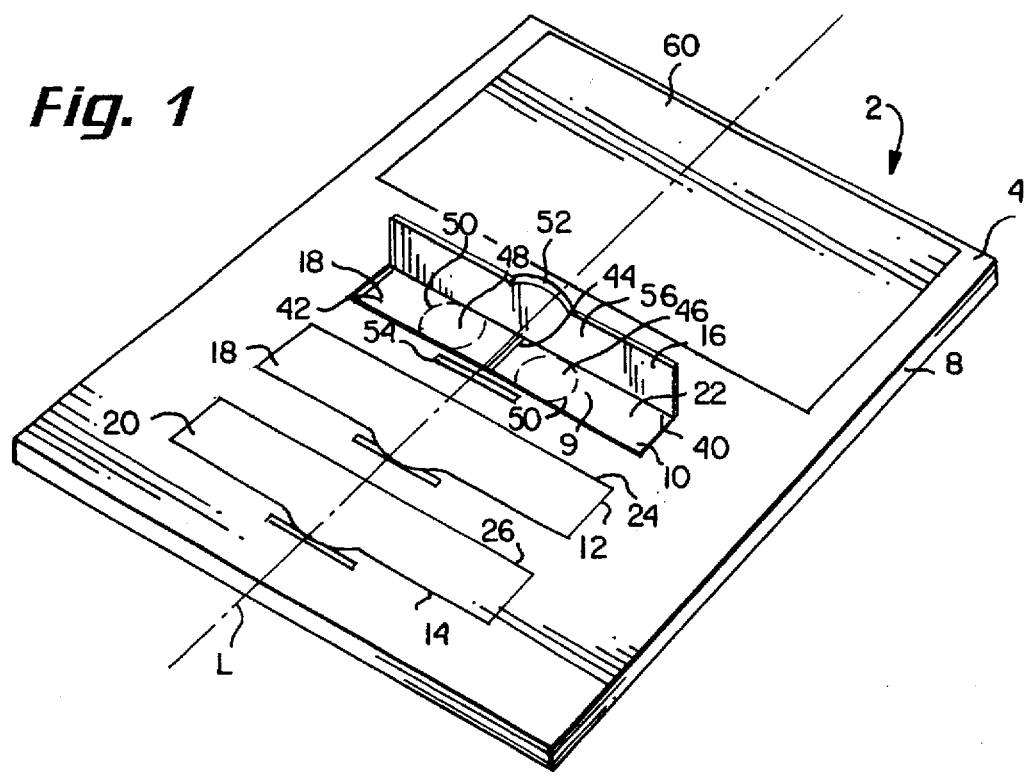
FIG. 1 is a perspective view of the device of the invention showing one cover in the open position.
Figure 2:
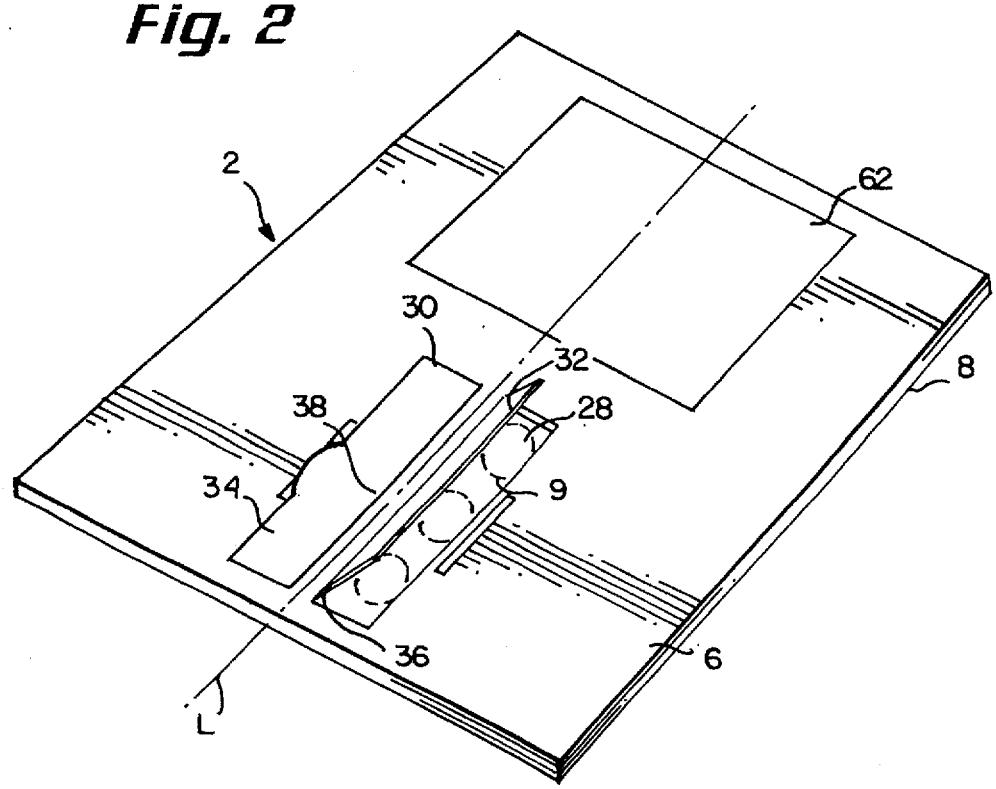
FIG. 2 is a perspective view of the device of FIG. 1 as viewed from the other side and showing one cover in the open position.

Referring to FIGS. 1-3, where like numbers refer to the same elements, a device of the invention, generally referenced 2, is shown which includes first and second panels 4, 6 with a support panel 8 disposed between the first and second panels 4, 6 carrying a absorbent sheet 9 on which a specimen is placed. The first panel 4 has three rectangular apertures 10, 12, 14 extending transversely of a longitudinal axis L of the first panel. Each aperture has a respective cover 16, 18 and 20 hingedly mounted to the first panel along a hinge line 22, 24, 26 extending transversely of the longitudinal axis L. Each cover 16, 18, 20 is hingedly movable independently of the other between a closed position as shown for covers 18 and 20 where the cover overlies the aperture, and an open position as shown for cover 16 where the aperture 10 and underlying sheet 9 are exposed.

The second panel 6 includes two rectangular apertures 28, 30 extending longitudinally of the longitudinal axis L and positioned opposite the transversely extending apertures 10, 12, 14 in the first panel 4. Aperture 28 is provided with a cover 32 and aperture 30 is provided with a cover 34. Covers 32 and 34 are each hingedly mounted along a respective hinge line 36, 38, each of which extends parallel to longitudinally axis L of second panel. Each cover 32, 34 is movable independently of each other between a closed position as shown for cover 34 where the cover overlies the aperture 30, and an open position as shown for cover 32 where the aperture 28 and underlying sheet 9 are exposed.

The support panel 8 is positioned between the first and second panels 4, 6 and supports sheet 9. Sheet 9 is made of an absorbent material, and is typically filter paper impregnated with a reagent which will react with hemoglobin components from blood and a peroxide solution to form a colored compound. Examples of suitable reagents are guaiac, tetramethyl benzidene, orthotoluidine and other similar chromogens. In the embodiment illustrated herein, the reagent impregnated in sheet is guaiac. The support panel 8 has apertures 11 corresponding to the apertures in the first panel.

Figure 3A:
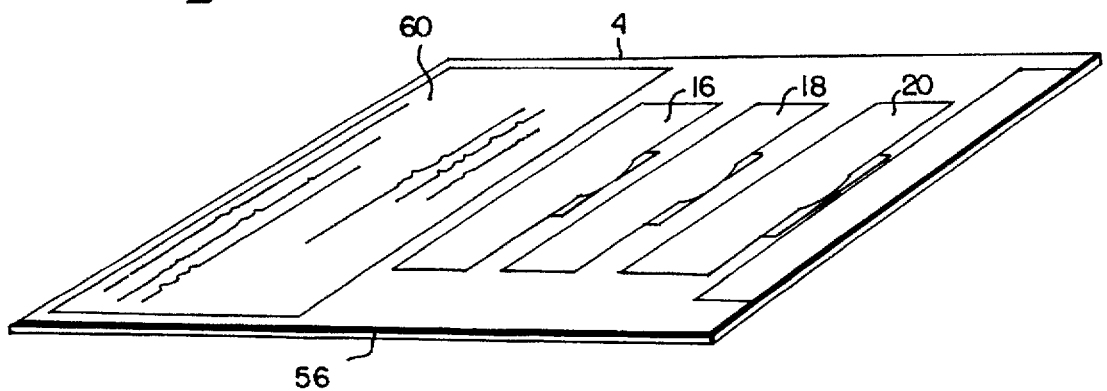
FIGS. 3a, 3b and 3c are an exploded view of the device of FIG. 1 showing the outer panels and the support panel carrying the sheet therebetween.
Figure 3B:
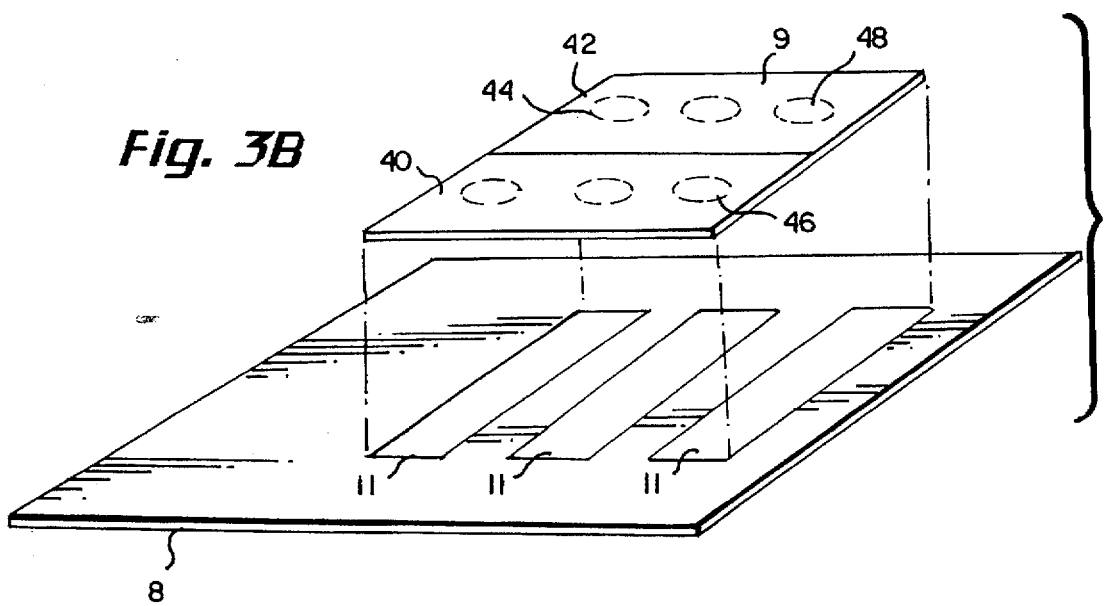
Figure 3C:
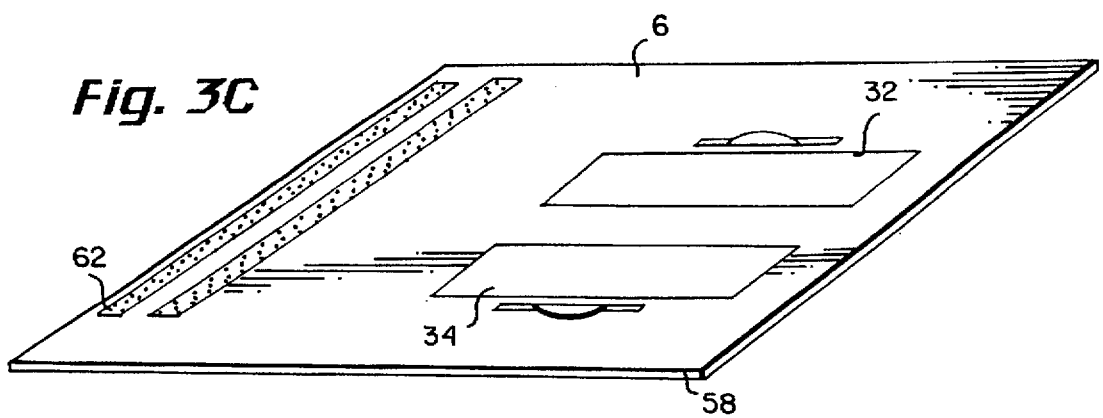

Referring to FIG. 3, FIGS. 3a and 3c show the first and second panels 4, 6 with the respective first and second covers overlying the apertures. In FIG. 3c, the second panel is oriented upwards for ease of viewing. FIG. 3b shows sheet 8 disposed between panels 4 and 6. In the embodiment illustrated, the sheet 9 is a single piece of filter paper having first and second portions 40, 42 separated from each other by a dividing region 44, which may comprise a hydrophobic material, for example wax. The first portion 40 is impregnated with the reagent and the second portion 42 is not impregnated with reagent. It is possible however for both portion to be impregnated with reagent provided impregnation of the second portion does not adversely affect any subsequent testing which might be conducted using the second portion. The first and second portions are visible through the apertures when the respective covers are in the open position. Each of the portions 40, 42 is provided with indicating means 46, 48, typically circular zones in dashed outline, in order to assist the user in knowing where to smear sample on the sheet. Moreover, the zones 48 have perforations 50 to enable the zones 48 to be removed from the sheet 9 for further analysis (described in more detail below).

The outer panels 4, 6 and the support panel 8 are preferably formed of paper or cardboard in which the apertures are die-cut along with perforations in the outer panels to form the covers. The panels could equally be made from other suitable materials such as a plastic material. A tab 52 is formed on each cover and is engageable with a slit 54 to maintain the cover in the closed position. The slit 54 may be formed during the die-cutting operation mentioned above.

The sheet 9 is typically cut from a length of filter paper with a repeating pattern of perforations 50 corresponding to the zones 48. The sheet 9 may be formed from one piece of filter paper with the hydrophobic dividing region 44 separating the first and second portions. Alternatively, the first and second portions may be two separate pieces of filter paper each constituting the first and second portions of the sheet, and separated by a hydrophobic region.

The device is assembled by overlying the panels 4 and 6 with the support panel 8 carrying the sheet 9 therebetween. The assembly is held together with a suitable glue or adhesive. In order to minimize sticking of the covers to the specimen, the panels 4 and 6 are provided on their inner surfaces 56, 58 with a layer of non-stick material, typically a wax layer. In this way, the perforated zones 48 carrying the specimen can be removed without them sticking to the inner surfaces of the covers on the first and second panels.

The panels 4, 6 and support panel 8 are assembled such that the apertures in the first panel and the support panel are opposite the apertures in the second panel, and the first and second portions on the sheet are aligned with the apertures in each panel. In this way, specimens placed on the sheet through the apertures in the first panel can be accessed and tested through the apertures in the second panel.

The first panel 4 may be provided with appropriate printed matter at the top and bottom to assist the user. For example, the patient's name, address and instructions on how to use the device may be printed at the top of the first panel in the region 60. Printed matter may also be provided at the top and bottom of the second panel. For example instructions to the doctor as to how to carry out testing by opening respective covers on the second panel 6 may be provided at 62.

In use, where a fecal sample is to be analyzed, a cover on the first panel 4 of the device is opened and a fecal specimen is smeared through the aperture on the first and second portions of the exposed sheet. The cover is then closed. A second fecal sample taken at a different time as a result of a different bowel movement is then smeared onto the first and second portions of the sheet through the second aperture on the first panel and the cover is closed. The third specimen from yet a different bowel movement at a different time is smeared onto the first and second portions through the third aperture on the first panel and the cover is closed. To conduct a first analysis, the cover on the second panel covering the first portions on which specimen has been applied is opened and developer solution is applied to the circular zone 46 of each first portion. If a specimen tests positive, as evidenced, for example, by the development of a blue color, the cover on the second panel covering the second portions is opened, and the respective perforated circular zone 48 of the second portion of the sheet carrying the positive specimen is removed from the sheet and subjected to further analysis (e.g. an immunochemical test).

Figure 4A:
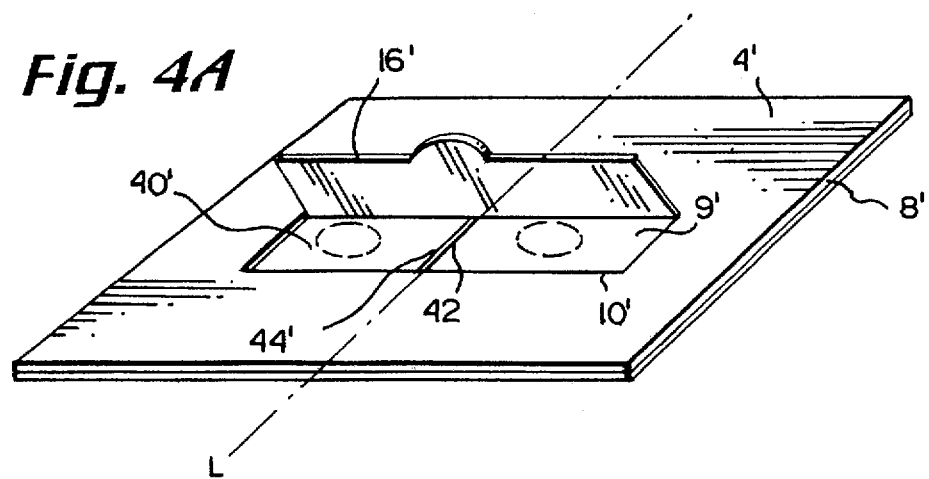
FIGS. 4a, 4b and 4c show perspective views of alternative embodiments of the device of the invention.
Figure 4B:
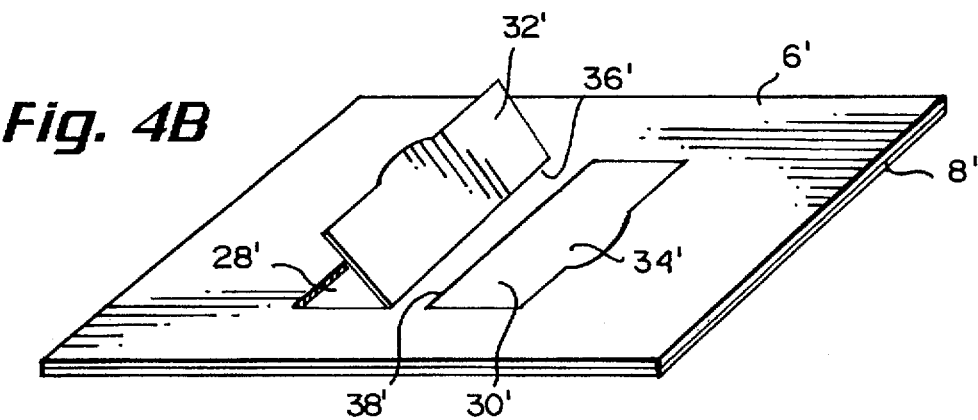

FIGS. 4a and 4b show an alternative embodiment of the device of the invention including a first panel 4' with one aperture 10' extending transversely of longitudinal axis L and a cover 16' overlying the aperture 10', a second panel 6' with two apertures 28', 30' each with an independently moveable cover 32', 34' hingedly mounted along hinge lines 36', 38' extending parallel to axis L, and a support panel 8' positioned between the first and second panels with a sheet 9' having first and second portions 40', 42' divided by a dividing region 44'. The covers on the first and second panels overlie the first and second portions 40', 42' of sheet 9'.

Figure 4C:
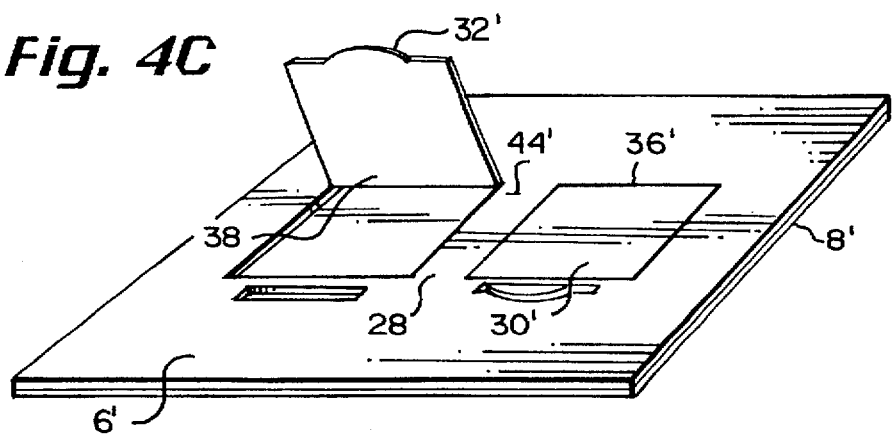

FIG. 4c shows a structural variation of the device of FIGS. 4a and 4b where the second panel 6' has a single transversely extending aperture 28' opposite the single aperture in the first panel with two independently moveable covers 30', 32' hingedly mounted along hinge lines 36', 38' extending transversely of axis L. The device of FIGS. 4a-4c is constructed and used in the same manner as for the embodiment described with reference to FIGS. 1-3, and is adapted for situations where it is not necessary to collect and analyze a plurality of specimens.

Further modifications of the invention will be readily apparent to those skilled in the art. For example, the invention has been described above with reference to the preferred embodiment where three transversely extending rectangular apertures are present in the first panel 4 and two longitudinally extending rectangular apertures are in the second panel 6. The invention, however, is not limited to devices comprising three apertures in the first panel. Embodiments comprising fewer apertures in the first and second panels are described above. Other embodiments with more or less than three apertures in the first panel may be constructed and used as the analytical situation demands.

In the above description, the apertures are illustrated as rectangular. However, any desired shape may be used, for example oval or circular.

The device has been described as including a support panel 8. However, it is possible, depending on the dimensions of the device and the thickness of the filter paper, to dispense with the support panel and place the sheet 9 directly between the first and second panels 4, 6.

The invention has been described with reference to analysis of fecal samples for stool occult blood. However, the device may be used for screening and testing of other biological specimens, for example blood and AIDS tests, urine tests and pregnancy tests.

While the present invention has been described in considerable detail, the invention disclosed herein is not limited to the detailed description, and is to be afforded the full scope of the appended claims and all equivalents thereto.

What is claimed is:

1. A specimen testing device, comprising:
    a first panel;
    a first and second aperture in said first panel;
    a second panel mounted opposite to said first panel;
    a third and fourth aperture in said second panel opposite said first and second apertures in said first panel, said first and second panels having a longitudinal axis;
    a sheet disposed between said first and second panels for receiving a specimen through said first and second apertures in said first panel, said sheet in each of said first and second apertures having first and second portions disposed on opposite sides of said longitudinal axis for receiving the specimen, said first portion containing a reagent for reaction with the specimen;
    a first aperture cover mounted on said first panel and overlying said first aperture in said first panel;
    a second aperture cover mounted on said first panel and overlying said second aperture in said first panel;
    a third aperture cover mounted on said second panel and overlying said first portion of said sheet;
    a fourth aperture cover mounted on said second panel and overlying said second portion of said sheet;
    said first and second aperture covers on said first panel being hingedly mounted along a hinge line extending transversely of said longitudinal axis;
    said third and fourth aperture covers on said second panel being hingedly mounted along a hinge line extending parallel to said longitudinal axis;
    wherein opening of said third aperture cover on said second panel exposes said first portion containing said reagent for reaction with said specimen, and opening of said fourth aperture on said second panel exposes said second portion for further analysis of the specimen received thereon.

2. A device according to claim 1, wherein said apertures in said first and second panels are rectangular.

3. A device according to claim 1, wherein said first and second portions are divided by a dividing region.

4. A device according to claim 3, wherein said dividing region comprises a hydrophobic strip.

5. A device according to claim 1, wherein said first and second portions are provided with indicating means for locating where the specimen is to be placed on the sheet.

6. A device according to claim 5, wherein at least one of said indicating means is comprised of a zone which is removable from said sheet.

7. A device according to claim 6, wherein said zone is defined by perforations.

8. A device according to claim 1, wherein said first panel has three apertures extending transversely of said longitudinal axis and said second panel has two apertures extending parallel said to said longitudinal axis, said apertures in said second panel being opposite said apertures in said first panel.

9. A device according to claim 1, wherein said first and second panels have printed matter thereon.

10. A device according to claim 1, wherein an inner surface of said first and second aperture covers on said first panel is provided with a non-stick wax layer.

11. A device according to claim 1 wherein said sheet is supported on a support panel disposed between said first and second panels.

12. A method of analyzing a specimen using a specimen testing device including a first panel; a first and second aperture in said first panel; a second panel mounted opposite to said first panel; a third and fourth aperture in said second opposite to said first and second apertures in said first and second apertures having first and second portions disposed on first panel, first and second panels having a longitudinal axis; a sheet disposed between said first and second panels for receiving a specimen through said first and second apertures in said first panel, said sheet in each of said opposite sides of said longitudinal axis for receiving the specimen, said first portion containing a first reagent for reaction with the specimen; a first aperture cover mounted on said first panel and overlying said first aperture in said first panel; a second aperture cover mounted on said first panel and overlying said second aperture in said first panel; a third aperture cover mounted on said second and and overlying said first portion of said sheet; a fourth aperture cover mounted on said second panel and overlying said second portion of said sheet; said first and second aperture covers on said first panel being hingedly mounted along a hinge line extending transversely of said longitudinal axis; said third and fourth aperture covers on said second panel being hingedly mounted along a hinge line extending parallel to said longitudinal axis; wherein opening of said third aperture cover on said second panel exposes said first portion containing said reagent for reaction with the specimen, and opening of said fourth aperture on said second panel exposes said second portion for further analysis of the specimen received thereon said method comprising:
  (a) obtaining the specimen;
  (b) opening the first aperture cover on said first panel to expose said first and second portions of said sheet;
  (c) smearing a portion of said specimen on said first and second portions of said sheet through said first aperture;
  (d) closing said first aperture cover to overlie said first aperture of said first panel;
  (e) opening said third aperture cover on said second panel to expose said first portion of said sheet carrying said specimen and said first reagent;
  (f) applying a second reagent to said exposed first portion of said sheet;
  (g) observing a color change corresponding to a positive test condition upon reaction of the first reagent with the specimen; and
  (h) selectively opening said fourth aperture cover on said second panel and removing said second portion of said sheet, wherein the specimen is subjected to further testing.

13. A method according to claim 12, wherein the specimen is a fecal specimen.

* * * * *